(12) United States Patent
Egawa et al.

(10) Patent No.: US 7,939,269 B2
(45) Date of Patent: May 10, 2011

(54) METHOD AND COMPOSITION FOR DETECTING CANCER BY MEANS OF DETECTION OF EPSTEIN-BARR VIRUS NUCLEAR ANTIGEN 2 COACTIVATOR P100

(75) Inventors: Shin Egawa, Sagamihara (JP);
Hidetoshi Kuruma, Yokohama (JP);
Hiroyuki Takahashi, Tokyo (JP); Koji Igarashi, Kawasaki (JP)

(73) Assignee: Tosoh Corporation, Shunan-shi (JP)

( * ) Notice: Subject to any disclaimer, the term of this patent is extended or adjusted under 35 U.S.C. 154(b) by 0 days.

(21) Appl. No.: 11/856,107

(22) Filed: Sep. 17, 2007

(65) Prior Publication Data

US 2008/0069819 A1 Mar. 20, 2008

(30) Foreign Application Priority Data

Sep. 15, 2006 (JP) ................................ 2006-250895
Feb. 28, 2007 (JP) ................................ 2007-049849

(51) Int. Cl.
*G01N 33/53* (2006.01)
*C12N 5/09* (2010.01)
*C07K 16/00* (2006.01)

(52) U.S. Cl. ....... 435/7.1; 435/330; 435/344; 530/387.1
(58) Field of Classification Search .................. None
See application file for complete search history.

(56) References Cited

U.S. PATENT DOCUMENTS 6,255,049 B1 * 7/2001 Fisher ................................ 435/6
2005/0014165 A1 1/2005 Lee et al.

FOREIGN PATENT DOCUMENTS

| JP | 2005-80524 | 3/2005 |
|---|---|---|
| WO | WO 2006/013013 A2 | 2/2006 |

OTHER PUBLICATIONS

Grinstein et al (2002) Cancer Research 62: 4876-4878.*
Tong et al (1995) Molecular and Cellular Research. 15 (9): 4735-4744.*
Campell (1984) General Properties and Application of Monoclonal Antibodies, pp. 1-32, in Monoclonal Antibody Technology, 1984, Elsevier Science Publishers.*
Paukku et al. Mol Endocrinol. Sep. 2003;17(9):1805-14.*
Febbo PG, Sellers WR. Use of expression analysis to predict outcome after radical prostatectomy. J Urol. Dec. 2003;170(6 Pt 2):S11-9; discussion S19-20.*
Lo, D. Quantitative analysis of Epstein-Barr Virus in plasma and serum. Ann NY Acad Sci. 2001. 945:68-72.*
Perkins et al. Analysis of Epstein-Barr virus reservoirs in paired blooc and breast cancer primary biopsy specimens by real time PCR.Breast Cancer Res. 2006;8(6):R70. p. 1-8.*
Hidetoshi Kuruma, et al. "High molecular mass proteome of androgen-independent prostate cancer" Proteomics, vol. 5 Wiley-VCH Verlag GmbH & Co. KGaA, Weinheim 2005, pp. 1097-1112.
Mark A. Rubin, MD, et al. "α-Methylacyl Coenzyme A Racemase as a Tissue Biomarker for Prostate Cancer" Journal of American Medical Association. vol. 287,No. 13, Apr. 2002, pp. 1662-1670.
H. J. Heidebrecht, et al., "p100: A Novel Proliferation-Associated Nuclear Protein Specifically Restricted to Cell Cycle Phases S, $G_2$, and M", Blood, XP 002462683, vol. 90, No. 1, Jul. 1, 1997, pp. 226-233.
Database Geneseq (Online). XP 002462689, Apr. 7, 2005 (US 2005/0014165 A1).

* cited by examiner

*Primary Examiner* — Bo Peng
*Assistant Examiner* — Michelle Horning
(74) *Attorney, Agent, or Firm* — Oblon, Spivak, McClelland, Maier & Neustadt, L.L.P.

(57) ABSTRACT

The present invention relates to a method for diagnosing cancer and a detection reagent based on detection of Epstein-Barr virus nuclear antigen 2 (EBNA2) coactivator p100 contained in a specimen, and a method for treating cancer by controlling expression of EBNA2 coactivator p100 protein or a gene thereof.

7 Claims, 12 Drawing Sheets

FIG.13
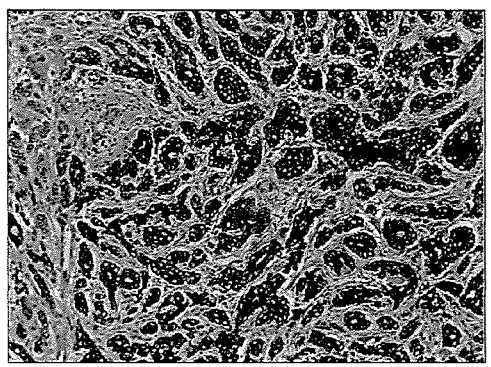
GLEASON PATTERN 5
GLEASON PATTERN 4
GLEASON PATTERN 3
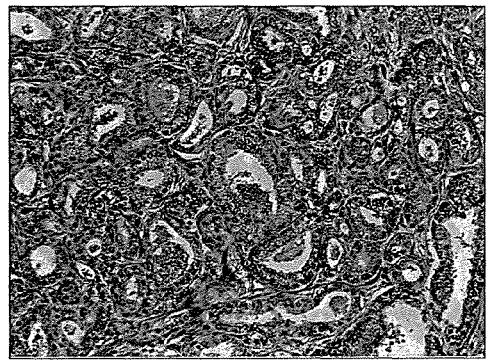
GLEASON PATTERN 2

FIG.16

| ORGAN | LESION | STAINING INTENSITY |
|---|---|---|
| LUNG | SQUAMOUS CELL CARCINOMA | 1 |
| ESOPHAGUS | SQUAMOUS CELL CARCINOMA | 0 |
| STOMACH | ADENOCARCINOMA | 1 |
| COLON | ADENOCARCINOMA | 2 |
| LIVER | HEPATOCELLULAR CARCINOMA | 0 |
| KIDNEY | CLEAR CELL CARCINOMA | 0 |
| BLADDER | UROTHELIAL CARCINOMA | 0 |
| PROSTATE | ADENOCARCINOMA | 2 |
| BREAST | DUCTAL CARCINOMA | 1 |
| OVARY | SEROUS PAPILLARY CARCINOMA | 0 |
| CERVIX | SQUAMOUS CELL CARCINOMA | 0 |
| SKIN | MELANOMA | 1 |
| BRAIN | ASTROCYTOMA | 1 |

SEQUENCE LISTING

```
<160> NUMBER OF SEQ ID NOS: 14

<210> SEQ ID NO 1
<211> LENGTH: 18
<212> TYPE: PRT
<213> ORGANISM: Homo sapiens
```

```
<400> SEQUENCE: 1

Arg Pro Ala Ser Pro Ala Thr Glu Thr Val Pro Ala Phe Ser Glu Arg
1               5                   10                  15

Thr Cys

<210> SEQ ID NO 2
<211> LENGTH: 14
<212> TYPE: PRT
<213> ORGANISM: Homo sapiens

<400> SEQUENCE: 2

Asp Asp Asp Ala Arg Thr Asp Ala Val Asp Ser Val Val Arg
1               5                   10

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
tcatcaagat ggtcctctca                                              20

<210> SEQ ID NO 4
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 4
cttaatacga ctcactatag ggtgcaatgt tttccccatt gg                     42

<210> SEQ ID NO 5
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 5
catggatcct atggcgtcct ccgcgcagag cggcg                             35

<210> SEQ ID NO 6
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 6
ggctctagac tagcggctgt agccaaattc gtctg                             35

<210> SEQ ID NO 7
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 7
catggatcca tggcgtcctc cgcgcagagc ggcg                              34

<210> SEQ ID NO 8
```

```
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 8
tcttcccaat aagcttttttt cgaag                                            25

<210> SEQ ID NO 9
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 9
aatttcttcg aaaaaagctt attgggaag                                         29

<210> SEQ ID NO 10
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 10
ggctctagac tagcggctgt agccaaattc gtctg                                  35

<210> SEQ ID NO 11
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 11
gggagaacac ccaggauaat t                                                 21

<210> SEQ ID NO 12
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 12
uuauccuggg uguucuccct t                                                 21

<210> SEQ ID NO 13
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
ccgcaaagca gaagaaagat t                                                 21

<210> SEQ ID NO 14
<211> LENGTH: 21
<212> TYPE: DNA
```

-continued

```
<213> ORGANISM: Artificial Sequence
<220> FEATURE:
<223> OTHER INFORMATION: Synthetic Polynucleotide

<400> SEQUENCE: 14
ucuuucuucu gcuuugcggt t                                              21
```

US 7,939,269 B2

METHOD AND COMPOSITION FOR DETECTING CANCER BY MEANS OF DETECTION OF EPSTEIN-BARR VIRUS NUCLEAR ANTIGEN 2 COACTIVATOR P100

TECHNICAL FIELD

The present invention relates to a method for diagnosing cancer and a detection reagent based on detection of Epstein-Barr virus nuclear antigen 2 (EBNA2) coactivator p100 contained in a specimen, and a method for treating cancer by controlling expression of EBNA2 coactivator p100 protein or a gene thereof.

BACKGROUND ART

Prostate specific antigen (PSA) is widely recognized to be an important marker of prostate cancer, and is currently widely used in general clinical medicine as well as testing and diagnostic applications. As a result, the frequency of detection of patients suspected of having prostate cancer is increasing. PSA exhibits abnormal values not only in prostate cancer but also in benign prostatic hypertrophy (BPH), thus making it difficult to diagnose prostate cancer on the basis of PSA alone. Although a comprehensive diagnosis is made, including rectal examination and diagnostic imaging, the final definitive diagnosis is made on the basis of a biopsy. Biopsy consists of a comprehensive diagnosis made on the basis of such factors as a cancer containment score of biopsied tissue, histopathological findings and PSA-related parameters. However, health care facilities do not have uniform diagnostic criteria for making these diagnoses, and studies are being conducted at numerous facilities for unifying diagnostic criteria even at present. One reason for this is the difficulty in making a histopathological assessment of prostate cancer. More specifically, although diagnosis of prostate tissue is made on the basis of disappearance of basal cells and confirmation of the presence of precancerous and cancerous lesions, since a subjective assessment by a pathologist has a considerable effect on the diagnosis, there is a need for a definitive tumor marker. Although cytoplasm staining marker 34βE12 and cell nucleus staining marker p63 are used in the staining of basal cells, these are not used to investigate the presence of cancer cells directly. Recently, a marker in the form of AMACR (α-methylacyl-CoA-racemase) has been developed that yields stained images specific for cancer cells. There have been numerous reports indicating the effectiveness of this marker for identifying cancer, and it has come to be used in the clinical setting. However, since this marker has unstable stained images and may also indicate a positive result for benign adenocarcinomas, it is not adequate for use as a tumor diagnostic marker by itself. A marker sought after in the clinical setting for diagnosis of prostate cancer is a testing reagent for cancers requiring aggressive treatment, or so-called clinically significant cancers. More specifically, this is a prostate cancer marker that yields stained images specific to advanced cancers only, but does not stain so-called clinically insignificant, latent cancers that are frequently observed in the elderly and do not require treatment. AMACR is unable to distinguish these cancer cells and ends up yielding a positive assessment even for prostate cancer not requiring treatment.

DISCLOSURE OF THE INVENTION

An object of the present invention is to provide a diagnostic marker sought after the most in the diagnosis of prostate cancer that is capable of specifically detecting only highly malignant prostate cancer requiring aggressive treatment without detecting insignificant cancers and other prostate cancer not requiring aggressive treatment. Moreover, another object of the present invention is to provide a method for treating cancer and therapeutic drug targeted at an antigen protein or gene thereof.

The present application includes the inventions indicated below.

[1] A method for detecting cancer by detecting Epstein-Barr virus nuclear antigen 2 coactivator p100 (EBNA2 coactivator p100).

[2] The detecting method of [1], wherein EBNA2 coactivator p100 is detected immunochemically using antibody to EBNA2 coactivator p100.

[3] The detecting method of [1] or [2], wherein the antibody is monoclonal antibody.

[4] The detecting method of any of [1] to [3], wherein the antibody at least recognizes an amino acid sequence of amino acids 423 to 440 consisting of RPASPATETVPAF-SERTC (SEQ ID NO. 1), an amino acid sequence of amino acids 806 to 819 consisting of DDDARTDAVDSVVR (SEQ ID NO. 2), or a partial sequence thereof, of EBNA2 coactivator p100 (Swiss Plot Accession No. Q7KZF4).

[5] The detecting method of any of [2] to [4], wherein the antibody is contacted with a specimen, and then the antibody that has bound to or has not bound to an antigen in the specimen is detected.

[6] The detecting method of any of [2] to [4], wherein the antibody is contacted with a specimen, and then an antigen that has bound to or has not bound to the antibody in the specimen is detected.

[7] The detecting method of any of [2] to [6], wherein the detection is carried out using any method selected from the group consisting of a competitive method using enzyme labeling, isotope labeling or fluorescent labeling, a sandwich method, a homogeneous assay method using fluorescence polarization, and a binding assay using surface plasmon resonance analysis.

[8] The detecting method of any of [2] to [7], wherein the detection is carried out by an immunohistochemical technique using enzyme labeling, isotope labeling or fluorescent labeling.

[9] The detecting method of any of [1] to [8], wherein the specimen used for the detection is a specimen containing human cells, human tissue or an extract thereof.

[10] The detecting method of any of [1] to [9], wherein the cancer is prostate cancer.

[11] The detecting method of any of [1] to [10], wherein the cancer is an advanced cancer not containing insignificant cancer.

[12] An EBNA2 coactivator p100 detecting reagent for carrying out the cancer detecting method of any of [1] to [11].

[13] The detecting method of [1], wherein the detection is via detection of EBNA2 coactivator p100 gene.

[14] The detecting method of [13], wherein the detection consists of detecting a gene amplification product by means of a polymerase chain reaction using a gene in a human specimen for the material.

[15] The detecting method of [13], wherein detection of the gene uses in situ hybridization on a human specimen.

[16] The detecting method of any of [13] to [15], wherein the cancer is prostate cancer.

[17] A reagent for detecting EBNA2 coactivator p100 gene for carrying out the cancer detecting method described in any of [13] to [16].

[18] A method for treating cancer using an antibody to EBNA2 coactivator p100.

[19] A method for treating cancer by controlling expression of EBNA2 coactivator p100 gene.

[20] The method of [19], wherein the control is based on specific knockdown of EBNA2 coactivator p100 gene.

[21] The method of [20], wherein the knockdown of a specific gene is carried out using siRNA.

[22] The method of any of [18] to [22], wherein the cancer is prostate cancer.

[23] A pharmaceutical composition for treating cancer comprising an antibody to EBNA2 coactivator p100.

[24] The pharmaceutical composition of [23], wherein the antibody is a monoclonal antibody.

[25] The pharmaceutical composition of [23] or [24], wherein the antibody at least recognizes an amino acid sequence of amino acids 423 to 440 consisting of RPASPATETVPAFSERTC (SEQ ID NO. 1), an amino acid sequence of amino acids 806 to 819 consisting of DDDARTDAVDSVVR (SEQ ID NO. 2), or a partial sequence thereof, of EBNA2 coactivator p100 (Swiss Plot Accession No. Q7KZF4).

[26] The pharmaceutical composition of any of [23] to [25], wherein the cancer is prostate cancer.

[27] The pharmaceutical composition of any of [23] to [26], wherein the cancer is an advanced cancer not containing insignificant cancer.

[28] A pharmaceutical composition for treating cancer comprising siRNA capable of controlling expression of EBNA2 coactivator p100 gene.

[29] The pharmaceutical composition of [28], wherein the cancer is prostate cancer.

According to the present invention, detection of cancer can be carried out by detecting EBNA2 coactivator p100 gene or protein. In particular, as a result of being able to diagnose the need for aggressive treatment in pathological diagnosis essential for definitively diagnosing prostate cancer by immunohistochemical staining with antibody recognizing amino acid nos. 423 to 440 or amino acid nos. 806 to 819 of the amino acid sequence of EBNA2 coactivator p100, the physical and mental burdens previously placed on patients due to unnecessary surgery and other treatment, as well as the economic burden in terms of health care costs and the like, can be expected to be reduced. Moreover, since the antigen of the present invention is a diagnostic marker that makes it possible to distinguish and diagnose benign prostatic hypertrophy (BPH), highly differentiated prostatic intraepithelial neoplasia and prostate cancer, and reflects the degree of malignancy by correlating with PSA concentration and Gleason score, it is able to provide a greater amount of clinical information required to determine the course of treatment. In addition, since the antigen of the present invention is also found in lung cancer, gastric cancer, colon cancer, breast cancer, skin cancer and brain tumor tissue, it can be expected to be used for pathological diagnosis of these diseases and as a therapeutic for these diseases, including prostate cancer.

BRIEF DESCRIPTION OF THE DRAWINGS

FIG. 13 shows immunohistochemically stained images of Gleason patterns 2 to 5 using EBNA2 coactivator p100.

FIG. 16 shows the results for a list of staining intensities during immunohistochemical staining of various cancer tissues with EBNA2 coactivator p100 antibody using a tissue array.

BEST MODE FOR CARRYING OUT THE INVENTION

Figure 1:
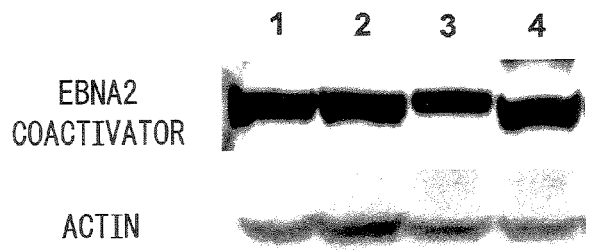
FIG. 1 shows the results of detecting androgen-dependent prostate cancer tissue (lanes 1 and 2) and non-androgen-dependent prostate cancer tissue (lanes 3 and 4) by Western blotting using anti-EBNA2 coactivator polyclonal antibody. The bottom of the drawing indicates the results for actin serving as an internal standard.

In addition to assessing for the presence or absence of cancer, the detection of EBNA2 coactivator p100 found by the inventors of the present invention enables specific detection of only cancer requiring treatment using immunohistochemical techniques and the like, and is expected to greatly contribute to the diagnosis of cancer, and particularly prostate cancer. EBNA2 coactivator p100 was identified as a transcription activity enhancer of Epstein-Barr virus nuclear antigen 2 in the form of a protein essential during transformation of Epstein-Barr virus to B lymphocytes (Tong, X., et al., Mol. Cell. Biol., 1995, 15, 4735). Its structure has four staphylococcal nuclease-like domains (SN-like domains) and a tudor domain (Callebaut, I., et al., Biochem. J., 1997, 321, 125), and it has been demonstrated to bind with signal transducer and activator of transcription 6 (STAT6) via an SN-like domain, bind with the large fragment of RNA polymerase II, and control the basal transcription mechanism of STAT6 by a bridging function (Yang, J., EMBO J., 2002, 21, 4950). In addition, it has also been demonstrated to have the ability to bind with c-Myb, a differentiation and growth factor of immature hematopoietic cells and lymphocytes, suggesting its involvement in translation activation (Leverson, J. D., Mol. Cell., 1998, 2, 417). Expression of EBNA2 coactivator p100 is unevenly distributed, taking place primarily in the cytoplasm within cells, but also being able to migrate to the nucleus, and has been indicated as having the potential to control translation activation (Ness, S. A., Oncogene, 1999, 18, 3039). Although these characteristics have been analyzed, their functions have yet to be elucidated, and there have been no reports regarding their correlation with cancer in particular.

Prostate cancer was found to be able to be detected by detecting EBNA2 coactivator p100 (Swiss Plot Accession No. Q7KZF4) in a specimen from human prostate tissue. In particular, the use of an antibody that specifically recognizes the region of amino acid nos. 423 to 440 or amino acid nos. 806 to 819, or a portion thereof, of the amino acid sequence thereof, and particularly an antibody that specifically recognizes a contiguous amino acid sequence thereof of 10 or more amino acids, and more preferably a contiguous amino acid sequence thereof of 15 or more amino acids, makes it possible to detect only malignant prostate cancer without cross-reacting with insignificant cancer not requiring aggressive treatment. In addition, similar effects can also be expected with a peptide or aptamer and the like, provided it has specific reactivity, without being limited to antibody.

Any means may be used to produce antibody provided it is an established technology. A full-length protein or partial region and so forth containing an amino acid sequence consisting of amino acid nos. 423 to 440 or amino acids 806 to 819 of EBNA2 coactivator p100 acquired in the form of a gene recombinant can be used as an immunoantigen, and a synthetic peptide may be used as the simplest method. Moreover, antibody production can also be induced by using a gene containing an EBNA2 coactivator p100 sequence, introducing into, for example, an animal cell expression vector, and expressing in an individual animal by administering a vector plasmid containing EBNA2 coactivator p100 to an animal. The host animal immunized with antigen can primarily be a mouse, rat, rabbit, goat or sheep and the like, and there are no particular limitations on host selection provided it is an antibody production system based on an established technology, including antibody production using chickens. When using a protein or peptide antigen, it is used to immunize an animal together with, for example, Freund's complete adjuvant, and by additionally repeating immunization with Freund's incomplete adjuvant as necessary, antibody titer can be expected to increase. Polyclonal antibody can be acquired by sampling serum from the animal, while monoclonal antibody can also be easily acquired by fusing the animal's B cells with a myeloma cell line.

As a specific example of the case of using a synthetic peptide as antigen, a synthetic peptide is produced from amino acids to which a cysteine residue has been added to the N-terminal or C-terminal of a synthetic peptide having an amino acid sequence consisting of amino acid nos. 423 to 440 or 806 to 819 and the like as necessary for the purpose of conjugating to a carrier protein serving as an immunogen. The synthetic peptide is purified by reverse phase high-performance liquid chromatography (HPLC) and the like followed by verifying the purity of the peptide with a mass spectrometry and confirming that the peptide demonstrates the target molecular weight to acquire the synthetic peptide as antigen. The synthetic peptide can be used by conjugating with a carrier protein serving as an immunogen such as Keyhole Limpet Hemocyanine (KLH) subjected to activation treatment with a maleimide group. A rabbit may then be immunized with the antigen together with Freund's complete adjuvant followed by several rounds of repeated administration with Freund's incomplete adjuvant at two week intervals. Serum is then collected from the animal two weeks after the final immunization, thereby enabling recovery in the form of anti-EBNA2 coactivator p100 polyclonal antibody.

Acquisition of the target antibody in the form of EBNA2 coactivator p100 antibody from the collected antiserum can be carried out by purifying the antiserum by ammonium sulfate precipitation, protein A or protein G, followed by concentrating the target antibody by affinity purification using beads or other support having antigen peptide immobilized thereto as necessary.

The use of this antibody makes it possible to detect EBNA2 coactivator p100 by, for example, immunohistochemical staining. Production of monoclonal antibody is carried out by immunizing an animal following the same procedure until antigen immunization. The animal is immunized with antigen without mixing with adjuvant three days prior to cell fusion, B cells are recovered from the animal's spleen and/or lymph nodes, and cell fusion with myeloma cells is carried out in accordance with ordinary methods. After selecting the fused cells using HAT medium and the like, antibody titer in the culture supernatant is confirmed by enzyme-linked immunosorbent assay (ELISA) and the like to select antibody-producing cell lines. Finally, hybridoma, monoclonal antibody-producing cell lines can be cloned and established by limited dilution method, and anti-EBNA2 coactivator p100 antibody can be acquired from a hyridoma culture supernatant thereof.

EBNA2 coactivator p100 in a specimen can be qualitatively or quantitatively detected by a method commonly known among persons with ordinary skill in the art such as a competitive method using enzyme labeling, isotope labeling or fluorescent labeling, sandwich method, homogeneous assay method using fluorescence polarization or a binding assay using surface plasmon resonance analysis, using the aforementioned monoclonal antibody or polyclonal antibody. In addition, similar effects can be expected with a peptide or aptamer and the like instead of using antibody provided it is a substance having specific binding properties.

Expression of EBNA2 coactivator p100 mRNA in cancer cells can be confirmed by in situ hybridization using a cRNA probe. More specifically, a PCR product can be acquired and purified after amplifying EBNA2 coactivator p100 gene by RT-PCR with a One-Step RT-PCR Kit (Qiagen) using 5'-tcatcaagatgg tcctctca-3' (SEQ ID NO. 3) (complementary sequence 5'-atggtcctctca-3': translation gene sequence 1-12) and 5'-cttaatacgactcactataggtgcaatgttttccccattgg-3' (SEQ ID NO. 4) (complementary sequence 5'-tgcaatgttttccccattgg-3': translation gene sequence 278-297) in which a T7 promoter sequence has been added to a complementary primer sequence to EBNA2 coactivator p100. The PCR product may be transcribed in vitro using a DIG RNA Labeling Kit (Roche) to produce a cRNA probe for detection of EBNA2 coactivator p100. After removing the paraffin from paraffin-embedded sections fixed with 10% formalin with xylene and a decreasing ethanol series, the specimen can be activated with 10 µg/mL of proteinase K and then fixed with 4% paraformaldehyde followed by treating with 0.2 N HCl and 0.25% acetic anhydride/triethanolamine. After carrying out intrinsic peroxidase deactivation treatment using 3% aqueous hydrogen peroxide and subjecting to an increasing ethanol series, the product is air-dried to obtain a specimen. The previously prepared cRNA probe is allowed to react overnight at 50° C., and after carrying out blocking treatment with a buffer containing 0.5% casein, rabbit F(ab') DIG/HRP antibody (dilution: 400×, Dako Japan) may be reacted for 15 minutes. After treating with biotinyl tyramide, the resulting product is then reacted with streptoavidin-HRP (dilution: 500×, Dako Japan) and can be visualized with diaminobenzidine (Dako Cytomation). Stained images can be observed after nuclear staining with hematoxylin and rinsing with running water followed by carrying out dehydration, penetration and sealing procedures. Since this mRNA is expressed specific to prostate cancer, it provides a useful technique for assessing the presence or absence of cancer cells.

Any means can be used for immunohistochemical staining using anti-EBNA2 coactivator p100 antibody provided it is an established technology. For example, a specimen of prostate cancer tissue obtained by surgery that has been fixed with formalin and embedded in paraffin is treated with xylene and a decreasing ethanol series to remove the paraffin followed by boiling for 10 minutes in 10 mM citrate buffer (pH 6.0) using a microwave oven to activate the antigen. The tissue sample and anti-EBNA2 coactivator p100 antibody are then reacted overnight at 4° C. followed by reacting with peroxidase-labeled secondary antibody to detect EBNA2 coactivator p100 antibody bound to the antigen and staining with diaminobenzidine. Since only malignant tumors are specifically stained during immunohistochemical staining carried out using antibody to amino acid sequence 423 to 440, while stained images of insignificant cancer are not observed, the presence or absence of cancer cells can be determined by immunohistochemical staining using anti-EBNA2 coactivator p100 antibody. Moreover, since insignificant cancers are not stained while only stained images of highly malignant cancer cells are obtained as a result of using antibody to amino acid sequence 423 to 440, a detecting method is provided that is extremely useful for diagnosing prostate cancer requiring aggressive treatment.

Since differences are observed in mRNA expression between insignificant cancer and highly malignant cancer cells based on the results of in situ hybridization, EBNA2 coactivator p100 detectable with antibody to amino acid sequence 423 to 440 is presumed to be present only in highly malignant cancer cells. Possible reasons for this include translation not occurring within the region of amino acid sequence 423 to 440 specific to insignificant cancer or in the vicinity of that region, modification of this region following translation, cleavage of this region following translation, large differences in intracellular localization, and this region undergoing a structural change caused by modification at another site within the protein, thereby preventing antibody binding.

The present invention also provides a method and pharmaceutical composition for treating cancer by inhibiting the activity of EBNA2 coactivator p100 and/or knocking down the expression of EBNA2 coactivator p100 gene, and deactivating expressed protein. Inhibition of EBNA2 coactivator p100 activity preferably uses an antibody that specifically binds with EBNA2 coactivator p100 and neutralizes the activity thereof, and more particularly, an antibody that specifically recognizes the amino acid sequence of amino acid nos. 423 to 440 described above, or a partial sequence thereof, preferably an antibody that specifically recognizes a contiguous amino acid sequence thereof of 10 or more amino acids, and more preferably an antibody that specifically recognizes a contiguous amino acid sequence thereof of 15 or more amino acids. In addition, similar effects can be expected with peptides and aptamers having similar reactivity without being limited to antibody. Although knockdown of EBNA2 coactivator p100 gene can be achieved by various genetics technologies such as RNA interference, antisense RNA-DNA, peptide and RNA-DNA aptamers, site-specific deletion, homologous recombination, dominant negative allele or intrabodies, knockdown by RNA interference is particularly preferable. RNA interference consists of inhibiting expression of a target gene by inserting into cells a double-strand RNA composed of a strand containing a sense oligonucleotide of about 21 to 23 nucleotides homologous to a portion of mRNA encoding a portion of the target gene, and a strand containing an antisense oligonucleotide of about 21 to 23 nucleotides homologous to a portion of the aforementioned mRNA. This method is based on interference specificity of double-strand RNA originating in a region encoding a gene, has been demonstrated to have superior usefulness in genetic research on nematodes (Fire, et al., Nature, 1998, 391, 806-811), and can be used for produce functionally-deficient phenotypes in fruit flies and mammals.

According to the present invention, the presence or absence of prostate cancer cells can be assessed by confirming the presence of EBNA2 coactivator p100 in tissue and particularly prostate cancer tissue. Moreover, immunohistochemical staining with antibody recognizing an amino acid sequence containing amino acid nos. 423 to 440, or a partial sequence thereof, makes it possible to specifically detect only highly malignant prostate cancer cells requiring aggressive treatment, thereby making it possible to improve the diagnostic accuracy of prostate cancer requiring aggressive treatment, and thus can be expected to greatly contribute to determination of the course of treatment. In addition, since expression of EBNA2 coactivator p100 gene has been confirmed not only in prostate cancer but also in a wide range of various other organs, it is expected to be able to be widely applied in not only the diagnosis of cancer, but also the diagnosis of cancer requiring biopsy. More specifically, since the expression thereof has been confirmed in lung cancer, gastric cancer, colon cancer, breast cancer, skin cancer and brain tumors by immunohistochemical staining of cancerous and tumor tissue with respect to normal tissue, it can be expected to be applied to the diagnosis and treatment of these cancers.

EXAMPLES

Example 1

Preparation of EBNA2 Coactivator p100 Antibody

A peptide of EBNA2 coactivator p100 amino acid sequence 423 to 400 (RPASPATETVPAFSERTC) (SEQ ID NO. 1) was synthesized and bound with maleimide-activated KHL using a cysteine residue for use as an immunogen followed by subcutaneously inoculating into a rabbit with adjuvant eight times at two week intervals. After collecting whole serum, the titer of the target antibody in the antiserum was confirmed as the reactive titer with antigen peptide by enzyme-linked immunosorbent assay (ELISA). In order to purify the target antibody from the antiserum, the antiserum was precipitated and concentrated with 50% saturated ammonium sulfate followed by recovery of the IgG fraction with a protein G-immobilized column. Moreover, the target antibody was purified and acquired by affinity purification with a column immobilized with antigen peptide, and the resulting target antibody was used in the following experiments.

Example 2

Detection of Antigen in a Cancer Cell Lines by Western Blotting Analysis Using Anti-EBNA2 Coactivator Antibody Androgen-dependent and non-androgen-dependent prostate cancer cells were prepared for use as cancer cell lines. Commercially available LNCaP cell line (American Type Culture Collection (ATCC), Rockville, Md., USA) were used as androgen-dependent human prostate cancer cells, and said LNCaP cell line was maintained and cultured in culture medium containing 10% fetal bovine serum (e.g., Roswell Park Memorial Institute (RPMI) medium) followed by mixing $1 \times 10^7$ of the cultured LNCaP cells with 0.1 mL of MATRIGEL™(Becton Dickinson Labware, N.J., USA). The cells were subcutaneously inoculated into male nude mice (BALB/c strain) and the testes were excised when the resulting tumor reached 100 to 200 $mm^3$. Although the tumor temporarily reduced in size, it soon began to grow again. Tumors prior to testectomy at this time were used as androgen-dependent prostate cancer, while tumors that had resumed growth following testectomy were used as non-androgen-dependent prostate cancer. These cancer tissues were acquired from two mice each. After carrying out electrophoresis on the cancer tissues under reducing conditions, the tissues were transferred to a polyvinylidene fluoride membrane and detected by Western blotting with anti-EBNA2 coactivator polyclonal antibody. Those results are shown in FIG. 1. EBNA2 coactivator was detected to about the same degree in both androgen-dependent cancer tissue and non-androgen-dependent cancer tissue specimens. In addition, EBNA2 coactivator was not confirmed to undergo any large changes in the amount of expression accompanying acquisition of androgen dependence.

The results of carrying out detection with anti-EBNA2 coactivator polyclonal antibody are shown in the top of FIG. 1 with androgen-dependent cancer tissue (LNCap) in lanes 1 and 2 and non-androgen-dependent cancer tissue in lanes 3 and 4. The bottom of FIG. 1 shows the results of detecting actin as an internal standard for the purpose of confirming the absence of differences in the amount of sample used between each lane.

Example 3

Figure 2:
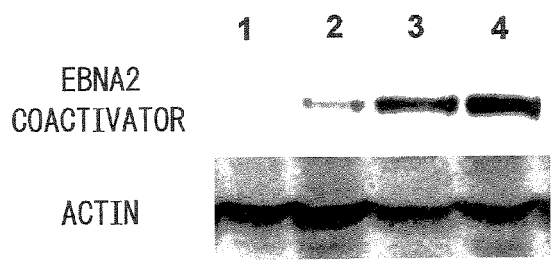
FIG. 2 shows the results of detecting normal tissue (lanes 1 and 2) and prostate cancer tissue (lanes 3 and 4) by Western blotting using anti-EBNA2 coactivator polyclonal antibody. The bottom of the drawing indicates the results for actin serving as an internal standard.

Detection of Antigen in Human Prostate Tissue By Western Blotting Using Anti-EBNA2 Coactivator Antibody Normal human prostate tissue and prostate cancer tissue were obtained from excised specimens from patients who underwent surgery. These specimens were mainly obtained from patients who underwent surgery in the department of urology of the Kitazato University Hospital located in Sagamihara City, Kanagawa Prefecture, Japan after having obtained their consent. Using two specimens or normal tissue and two specimens of prostate cancer tissue, detection was carried out in the same manner as Example 2 by Western blotting using anti-EBNA2 coactivator polyclonal antibody. Those results are shown in FIG. 2. An increased in the expressed amount was observed in the prostate cancer tissue as compared with the normal tissue.

The results of carrying out detection with anti-EBNA2 coactivator polyclonal antibody are shown in the top of FIG. 2 using normal tissue in lanes 1 and 2 and prostate cancer tissue in lanes 3 and 4. The bottom of FIG. 2 shows the results of detecting actin as an internal standard for the purpose of confirming the absence of differences in the amount of sample used between each lane.

Example 4

Detection of Expression of EBNA2 Coactivator Gene by RT-PCR

Figure 3:
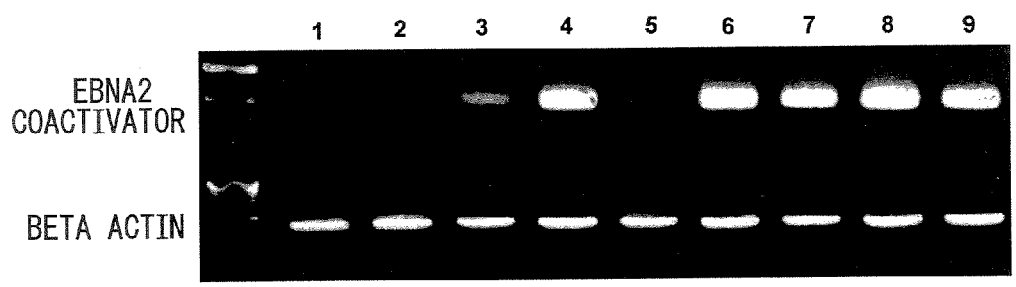
FIG. 3 shows the results of confirming the expression of mRNA of anti-EBNA2 coactivator by RT-PCR for normal human prostate tissue (lanes 1 to 3), human prostate cancer tissue (lanes 4 to 6) and a prostate cancer cell line (lanes 7 to 9). The bottom of the drawing indicates the results for actin serving as an internal standard.

The expressed amount of mRNA was confirmed by RT-PCR in three specimens of normal human prostate tissue, 3 specimens of human prostate cancer tissue and 3 specimens of prostate cancer cell line in the same manner as Example 3 using as primers 5'-tcatcaagatggtcctctca-3' (SEQ ID NO. 3) and 5'-cttaatacgactcactatagggtgcaatgttttccccattgg-3' (SEQ ID NO. 4). Those results are shown in FIG. 3. Strong expression of mRNA was confirmed in two of the prostate cancer tissue specimens, and expression of mRNA, although weak, was confirmed in one of the normal tissue specimens. In addition, strong expression of mRNA was confirmed in all samples of the prostate cancer cell line.

The results of confirming expression of mRNA by RT-PCR are shown in FIG. 3 using normal tissue in lanes 1 to 3, prostate cancer tissue in lanes 4 to 6, and prostate cancer cell line in lanes 7 to 9. The top of FIG. 3 shows results for the expression of mRNA by EBNA2 coactivator, while the bottom shows the results of detecting actin as an internal standard for the purpose of confirming the absence of differences in the amount of sample used between each lane.

Example 5

Detection of Expression of EBNA2 Coactivator Gene by In Situ Hybridization

Figure 4:
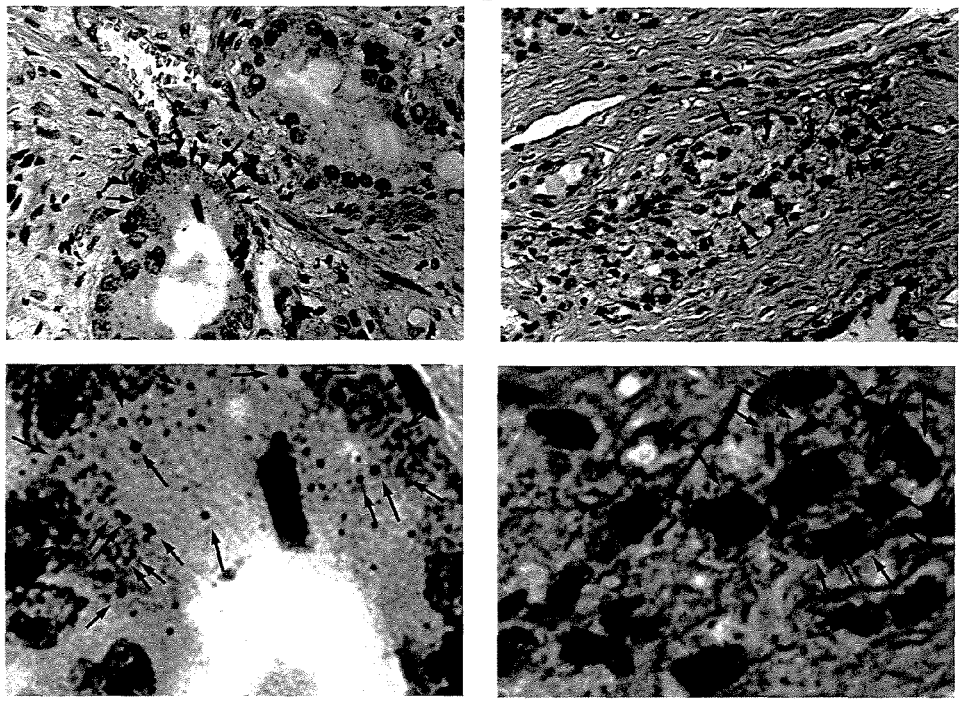
FIG. 4 shows the results of in situ hybridization of EBNA2 coactivator p100 gene in advanced cancer and insignificant cancer. The upper left image (magnification: 10×) and lower left image (magnification: 40×) shows the results for anti-EBNA2 coactivator p100 antibody. The arrows indicate stained images of typical cancer cells present in the field of view.

A PCR product was acquired and purified after having amplified EBNA2 coactivator P100 gene by RT-PCR with a One-Step RT-PCR Kit (QIAGEN®) using 5'-tcatcaagatggtcctctca-3' (SEQ ID NO. 3) and 5'-cttaatacgactcactatagggtgcaatgttttccccattgg-3' (SEQ ID NO. 4) in a T7 promoter sequence was added to primer sequence complementary to EBNA2 coactivator p100. The PCR product was transcribed in vitro using a DIG RNA Labeling Kit (Roche) to produce a cRNA probe for detection of EBNA2 coactivator p100. After removing the paraffin from paraffin-embedded sections fixed with 10% formalin by treating with xylene and a decreasing ethanol series, the PCR product was activated with 10 µg/mL of proteinase K and then fixed with 4% paraformaldehyde followed by treating with 0.2 N HC1 and 0.25% acetic anhydride/triethanolamine. After carrying out intrinsic peroxidase deactivation treatment using 3% aqueous hydrogen peroxide and subjecting to an increasing ethanol series, the PCR product was air-dried to obtain a specimen. The previously prepared cRNA probe was allowed to react overnight at 50° C., and after carrying out blocking treatment with a buffer containing 0.5% casein, rabbit F(ab') DIG/HRP antibody (dilution: 400×, Dako Japan) was reacted for 15 minutes. After treating with biotinyl tyramide, the specimen was then reacted with streptoavidin-HRP (dilution: 500×, DAKO Japan) and visualized with diaminobenzidine. Stained images were observed after nuclear staining with hematoxylin and rinsing with running water followed by carrying out dehydration, penetration and sealing procedures. Those results are shown in FIG. 4. Expression of mRNA was confirmed in cells of both advanced cancer and insignificant cancer. In addition, well-defined images of stained mRNA were not confirmed in the normal cells, thus confirming that this method is effective for detecting prostate cancer.

The upper left image (magnification: 10×) and the lower left image (magnification: 40×) show the results for advanced cancer, while the upper right image (magnification: 10×) and the lower right image (magnification: 40×) show the results for insignificant cancer. In both cases, images of stained mRNA (arrows) specific to cancer cells were confirmed by in situ hybridization. In addition, there were no differences observed in expression of mRNA between advanced cancer and insignificant cancer, with mRNA being localized in the cytoplasm in both cases.

Example 6

Figure 5:
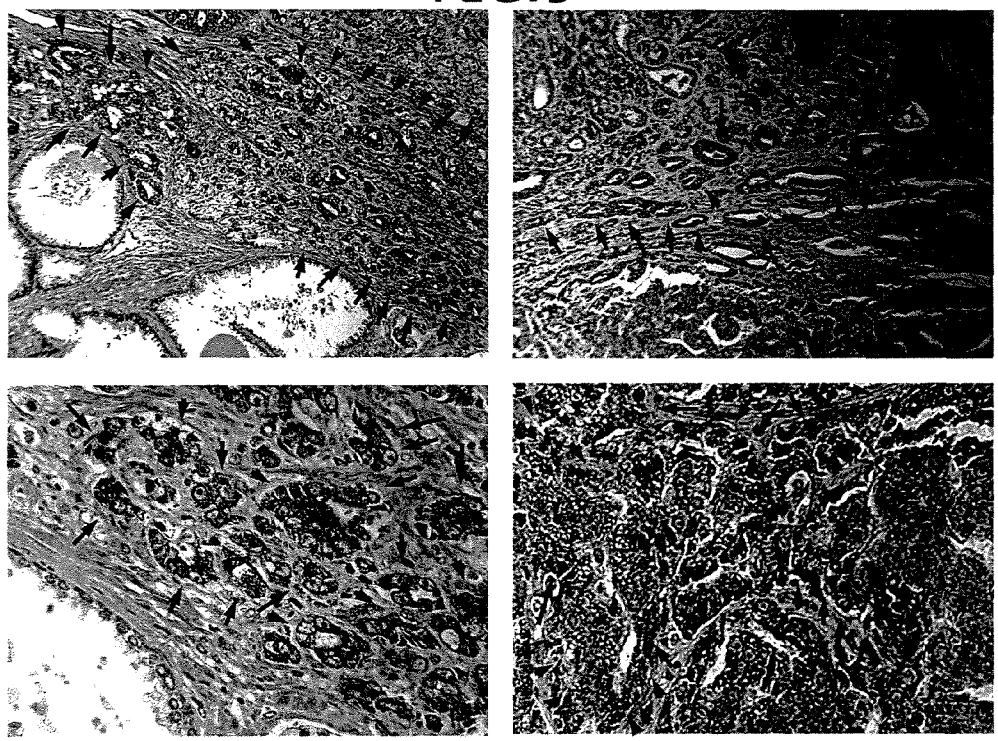
FIG. 5 shows detection of EBNA2 coactivator in advanced prostate cancer cells by immunohistochemical staining. The upper left image (magnification: 10×) and the lower left image (magnification: 40×) shows the results for anti-EBNA2 coactivator p100 antibody, while the upper right image (magnification: 10×) and lower right image (magnification: 40×) shows the results for AMACR antibody. The arrows indicate stained images of typical cancer cells present in the field of view.

Detection of EBNA2 Coactivator in Advanced Prostate Cancer Cells by Immunohistochemical Staining A specimen of prostate cancer tissue fixed with formalin and embedded in paraffin was removed of paraffin with xylene and a decreasing ethanol series followed by activating the antigen by boiling for 10 minutes in 10 mM citrate buffer solution (pH 6.0) using a microwave oven. The tissue sample, anti-EBNA2 coactivator p100 antibody and AMACR antibody (DAKO, P504S) were allowed to react overnight at 4° C., and after reacting with peroxidase-labeled anti-rabbit IgG antibody to detect antibody bound to the antigen, the samples were stained using DAB. Those results are shown in FIG. 5. Strongly stained images specific to prostate cancer cells were confirmed for both anti-EBNA2 coactivator p100 antibody and AMACR antibody in the advanced prostate cancer cells.

The upper left image (magnification: 10×) and the lower left image (magnification: 40×) show the results for anti-EBNA2 coactivator p100 antibody, while the upper right image (magnification: 10×) and the lower right image (magnification: 40×) show the results for AMACR antibody. Images of stained cytoplasm specific to prostate cancer cells were confirmed in both cases. Arrows indicate stained images of typical cancer cells present in the field of view.

Example 7

Figure 6:
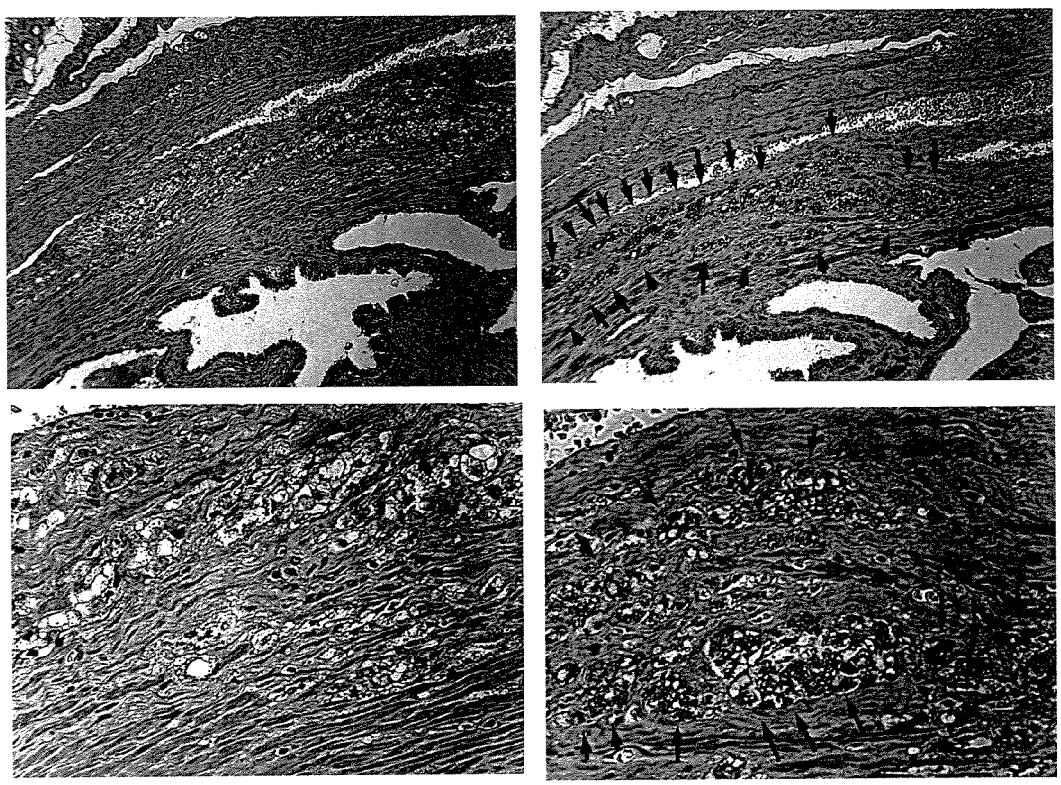
FIG. 6 shows detection of EBNA2 coactivator in insignificant prostate cancer cells by immunohistochemical staining. The upper left image (magnification: 40×) and lower left image (magnification: 120×) show the results for anti-EBNA2 coactivator p100 antibody, while the upper right image (magnification: 40×) and lower right image (magnification: 120×) show the results for AMACR antibody.

Detection of EBNA2 Coactivator in Insignificant Prostate Cancer Cells by Immunohistochemical Staining A prostate cancer tissue sample, anti-EBNA2 coactivator p100 antibody and AMACR antibody were allowed to react overnight at 4° C. in the same manner as Example 6, and after reacting with peroxidase-labeled anti-rabbit IgG antibody to detect antibody bound to antigen, the samples were stained using diaminobenzidine. Those results are shown in FIG. 6. Stained images were not observed with anti-EBNA2 coactivator p100 antibody in insignificant cancer cells in sections from the same patient, while strongly stained images specific to prostate cancer cells were only confirmed with AMACR antibody.

On the basis of these results and the results of Example 6, anti-EBNA2 coactivator p100 antibody was confirmed to specifically stain highly malignant cancer cells without staining insignificant cancer not requiring aggressive treatment.

The upper left image (magnification: 40×) and the lower left image (magnification: 120×) show the results for anti-EBNA2 coactivator p100 antibody, while the upper right image (magnification: 40×) and the lower right image (magnification: 120×) show the results for AMACR antibody. Stained images of cancer cells (arrows) were only confirmed for AMACR antibody in insignificant cancer, while stained images were not confirmed for anti-EBNA2 coactivator p100 antibody.

Example 8

Production of Anti-EBNA2 Coactivator p100 Monoclonal Antibody

An antigen bound to maleimide-activated KLH using cysteine residues of synthetic peptides consisting of CPASPATETVPAFSERT, in which cysteine was added to the amino terminal of EBNA2 coactivator p100 amino acid sequence 424 to 439 (PASPATETVPAFSERT) (SEQ ID NO. 1), and DDDARTDAVDSVVRC, in which cysteine was added to the carboxy residue of EBNA2 coactivator p100 amino acid sequence 806 to 819 (DDDARTDAVDSVVR) (SEQ ID NO. 2), was prepared as an antigen, while that bound to maleimide-activated BSA was used as a screening antigen. A 7-week-old female Wistar Lewis rat was immunized under ether anesthesia by administration of 250 µg of the peptide-added KLH antigen into the footpod together with Freund's complete adjuvant. One month later, the inguinal lymph nodes and mesenteric lymph nodes were excised from the rat followed by collection of B cells there from. Cell fusion was carried out in accordance with ordinary methods in the presence of mouse myeloma cell line PAI and polyethylene glycol, and selected by HAT medium for about 10 days. Cells in the positive screening wells were subjected to monoclonal conversion by limited dilution to establish the cells in the form of a hybridoma. At this time, after culturing in HT medium for about 10 days, culturing was finally continued in hybridoma medium, and the culture supernatant was recovered to collect the antibody. The medium consisted of hybridoma cell culturing medium prepared by adding 27.5 mL of NCTC-109 medium (Invitrogen), 5.5 mL of nonessential amino acids (Invitrogen) and 5.5 mL of pencillin/streptomycin/glutamic acid (Invitrogen) to 500 mL of GIT medium (Dainippon Sumitomo Pharma Co., Ltd.). HAT (Sigma-Aldrich Co., HYBRYMAX, Cat. No. H0262) was then added to this medium for use as HAT medium, while HT (Sigma-Aldrich Co., HYBRYMAX, Cat. No. H0137) was added for use as HT medium. Hybridoma screening was carried out coating a 96-well immunoplate (Griener, Cat. No. 655001) with peptide-conjugated BSA at 50 ng/well. More specifically, the peptide-conjugated BSA was diluted with TBS (10 mM Tris-HCl, 150 mM NaCl, pH 7.4) to prepare a 1 µg/mL solution. This solution was then added to an immunoplate at 50 µL/well and stored overnight at 4° C. Then, after washing three times with TBS, TBS solution containing 3% bovine serum albumin (BSA) was added at 250 µL/well followed by allowing to stand at room temperature for 2 hours. After washing four times with TBST (TBS containing 0.05% Tween 20), HRP-labeled anti-rat IgG antibody at 0.2 µg/mL in TBST containing 1% BSA were added at 50 µL/well followed by allowing to stand at room temperature for 2 hours. After washing four times with TBST and adding TMB substrate (Kirkegaard & Perry Laboratories, Inc., Cat. No. 50-76-00) at 50 µL/well and allowing to stand a room temperature for 30 minutes, the reaction was stopped with 1 N phosphoric acid followed by measurement of absorbance at 450 nm. Samples indicating a positive reaction were selected as positive clones, and monoclonal antibody was established by limited dilution.

Example 9

Cloning of EBNA2 Coactivator p100 Gene and Discovery in *Escherichia coli*

Figure 7:
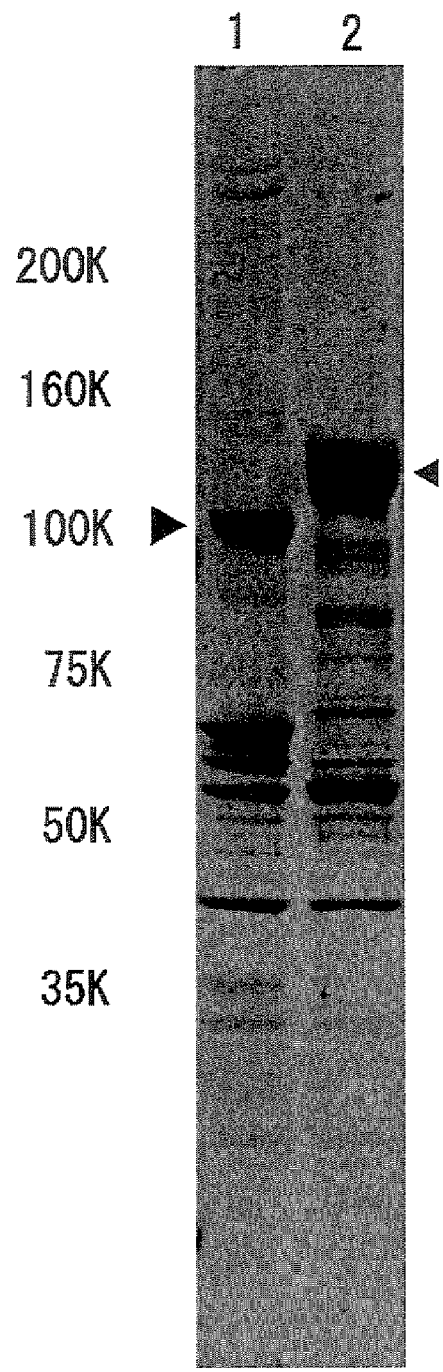
FIG. 7 shows pCold-EBF1 (lane 1) and pCold-EBF2 (lane 2) expressed in *Escherichia coli*. Arrows indicate target proteins.

LNCap cells were cultured in Dulbecco's Modified Eagle Media (Invitrogen) containing 5% FCS, 100 units/mL penicillin and 100 µg/mL streptomycin. Approximately 1 ×10$^7$ cells were recovered followed by recovery of RNA using the RNeasy Mini Kit ( QIAGEN®) in accordance with the manual. EBNA2 coactivator p100 was cloned by using for the 5'-side primer 5'-catggatccatggcgtcctccgcgcagagcggcg-3' (SEQ ID NO. 5), in which a BamHI cleavage sequence was added to a nucleotide sequence encoding EBNA2 coactivator p100, and using for the 3'-side primer 5'-ggctctagactagcggct-gtagccaaattcgtctg-3' (SEQ ID NO. 6), in which an XbaI cleavage sequence was added to a nucleotide sequence encoding EBNA2 coactivator p100, to prepare EBNA2 coactivator p100 cDNA using the OneStep RT-PCR Kit (QIAGEN®) in accordance with the manual. The prepared cDNA was cleaved using the restrictase BamHI and XbaI cleavage sites added to the primers, and ligated to the product of cleaving the multicloning sites BamHI and XbaI of pUC18 vector with the restrictases to prepare the target plasmid. The full-length sequence of the resulting EBNA2 coactivator p100 gene was confirmed with the ABI PRISM (registered trademark) 310 Genetic Analyzer (Applied Biosystems). Primers consisting of 5'-catggatccatggcgtcctccgcgcagagcggcg-3' (SEQ ID NO. 7) and 5'-tcttcccaataagcttttttcgaag-3' (SEQ ID NO. 8) corresponding to amino acid residues 1 to 410 of the amino acid sequence of EBNA2 coactivator p100, and primers consisting of 5'-aatttcttcgaaaaaagcttattgggaag-3' (SEQ ID NO. 9) and 5'-ggctctagactagcggctgtagccaaattcgtctg-3' (SEQ ID NO. 10) corresponding to amino acidresidues 411 to 910 of the amino acid sequence of EBNA2 coactivator p100, were used to acquire a target gene fragment for the purpose of expressing protein in *Escherichia coli*. PCR was carried out using pUC18 containing EBNA2 coactivator p100 gene as a template to obtain gene fragments EBF1 (corresponding to amino acid residues 1 to 410) and EBF2 (corresponding to amino acid residues 411 to 910). After carrying out restriction enzyme digestion on the resulting PCR products of EBF1 and EBF2 with BamHI/HindIII and HindIII/XbaI, respectively, the PCR products were introduced by ligation into a pCold TF vector similarly subjected to restriction enzyme diagestion with BamHI/HindIII and HindIII/XbaI. After confirming the gene sequences, the resulting pCold-EBF1 and pCold-EBF2 plasmids were transformed in *Escherichia coli* strain JM109, and protein was expressed. Protein was expressed by culturing the *Escherichia coli* transformed with pCold-EBF1 and pCold-EBF2 in LB medium containing 50 µg/mL ampicillin at 37° C. to an absorbance at 600 nm of 0.5. Subsequently, after allowing to stand undisturbed for 30 minutes at 15° C., isopropyl-β-D-thiogalactopyranoside was added to a final concentration of 1 mM followed by culturing for 24 hours at 15° C. Following completion of culturing, the *Escherichia coli* were recovered by centrifugation, and after subjecting to ultrasonic treatment in TBS (10 mM-Tris-HCl, 150 mM NaCl, pH 7.4) containing 4 mM phenylmethylsulfonyl fluoride and 0.1% Tween 20, the solution fraction was recovered by centrifugation. Since the EBNA2 coactivator fragments are expressed in the form of a fused protein with a trigger protein having a polyhistidine sequence, it is able to be purified with a metal chelating column using polyhistidine. More specifically, precipitate consisting of cell fragments and other matter was removed from the solution fragment with a 0.45 µm filter. 5 mL of 50 mM NiCl$_2$ solution were added to a HiTrap™Chelating HP (GE Healthcare) to bind the nickel. After washing with 15 mL of pure water, the column was equilibrated with 20 mM phosphate buffer (pH 7.4) containing 0.5 M NaCl and 0.1% Tween 20. The sample containing the target protein was loaded onto the column after adjusting to pH 7.4 with 20 mM phosphate buffer containing 0.5 M NaCl and 0.1% Tween 20. Unbound substances were washed with a washing solution of 20 mM phosphate buffer (pH 7.4) containing 0.5 M NaCl, 10 mM imidazole and 0.1% Tween 20, and the absorbance at 280 nm of the solution passing through the column was confirmed to be 0.01 or less. The target substances were then eluted from the column with 20 mM phosphate buffer (pH 7.4) containing 0.5 M NaCl, 500 mM imidazole and 0.1% Tween 20. Since the purified proteins are in the form of fused proteins consisting of the target proteins in the form of EBF1 (molecular weight: 46 kDa) and EBF2 (molecular weight: 56 kDa) with the trigger protein (molecular weight: 52 kDa), the molecular weights were predicted to be 98 kDa and 108 kDa, respectively, and the predicted molecular weights were confirmed to be demonstrated by SDS-PAGE. Those results are shown in FIG. 7.

Example 10

Figure 8:
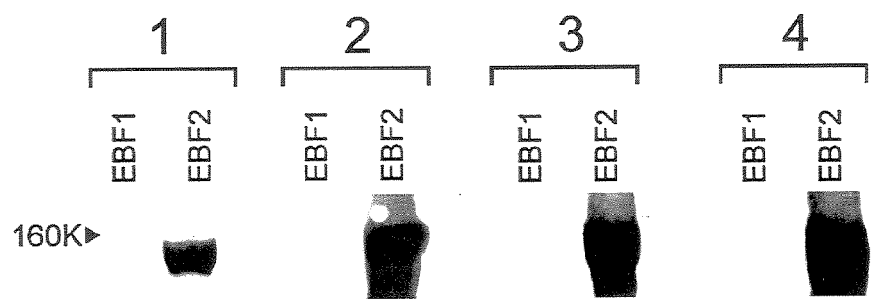
FIG. 8 shows the reactivity of antibody to pCold-EBF1 and pCold-EBF2. The results are shown for antibodies 1 to 4 consisting of 1: clone name EB2.15as monoclonal antibody (recognizing amino acid sequence 806 to 819: DDDARTDAVDSVVR), 2: clone name EB3C.2a monoclonal antibody (recognizing amino acid sequence 424 to 439: PASPATETVPAFSERT), 3: EB2 polyclonal antibody (recognizing amino acid sequence 806 to 819: DDDARTDAVDSVVR), and 4: EB3 polyclonal antibody (recognizing amino acid sequence 423 to 439: RPASPATETVPAFSERT).

Reactivity of EBNA2 Coactivator p100 Antibody to *Escherichia coli*-Expressed Protein The reactivity of antibody to pCold-EBF1 and pCold-EBF2 expressed in *Escherichia coli* was analyzed by Western blotting. After carrying out SDS-PAGE under reducing condition on the purified protein at 1 µg/lane, the purified proteins were transferred to a PVDF membrane followed by carrying out blocking treatment overnight with TBS containing 3% skim milk. After washing with TBS and reacting for 2 hours with 1% Blockace-TBST containing 1 µg/mL of anti-EBNA2 coactivator p100 antibody, 1% Blockace-TBST containing 0.3 μg/mL alkaline phosphatase-labeled anti-rat IgG antibody (American Qualex: Cat. No. A103AT) or 1% Blockace-TBST containing 0.3 μg/mL alkaline phosphatase-labeled anti-rabbit IgG antibody (Zymed) was added. After reacting for 2 hours and adequately washing with TBST, the development of color was detected with NBT/BCIP (Pierce). Those results are shown in FIG. 8. According to these results, both polyclonal antibody and monoclonal antibody were confirmed to demonstrate strong reactivity with EBNA2 coactivator p100.

Example 11

Figure 9:
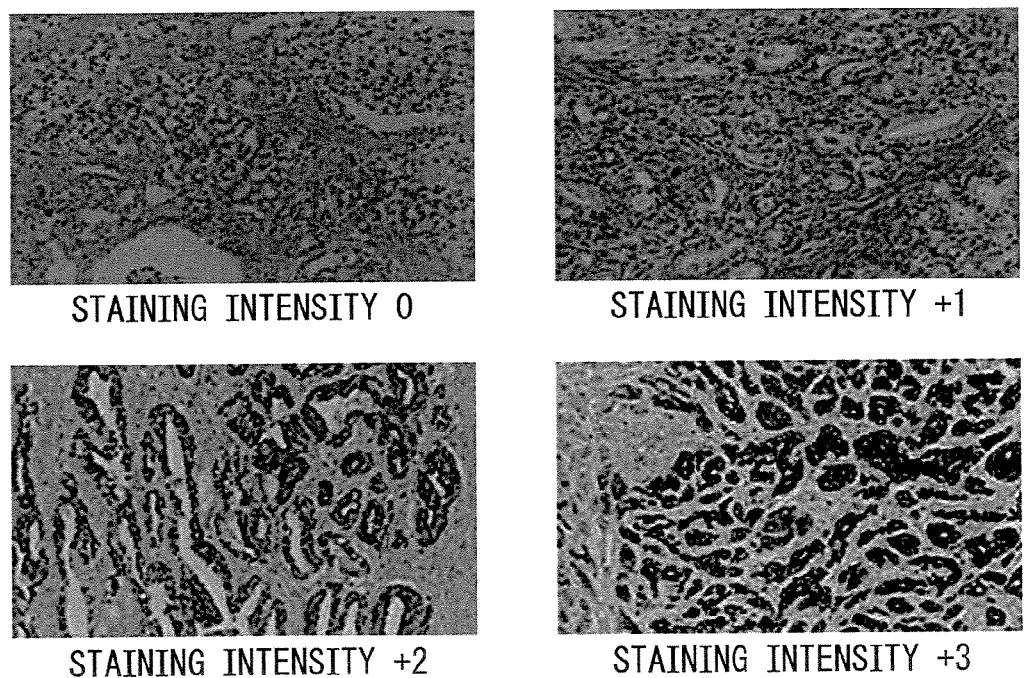
FIG. 9 shows immunohistochemical staining intensities attributable to EBNA2 coactivator p100 polyclonal antibody. Staining intensity was classified to one of four levels consisting of staining intensity 0 (no staining), staining intensity +1 (weak staining), staining intensity +2 (moderate staining) and staining intensity +3 (strong staining).

Comparison of EBNA2 Coactivator p100 and AMACR by Prostate Immunohistochemical Staining Immunohistochemical staining of various prostate cancer pathological samples was carried out in accordance with Example 6 using polyclonal antibody acquired in Example 1 and commercially available AMACR antibody (Dako, P504S) to investigate the correlation with pathology in patients from which specimens were acquired. As shown in FIG. 9, immunohistochemical staining was classified to one of four levels consisting of 0 (no staining), +1 (weak staining), +2 (moderate staining) and +3 (strong staining), and the results of comparatively verifying the causative relationships with pathological diagnosis classification, PSA concentration, Gleason score and pathological T stage classification are shown by comparing EBNA2 coactivator p100 and AMACR.

Figure 10:
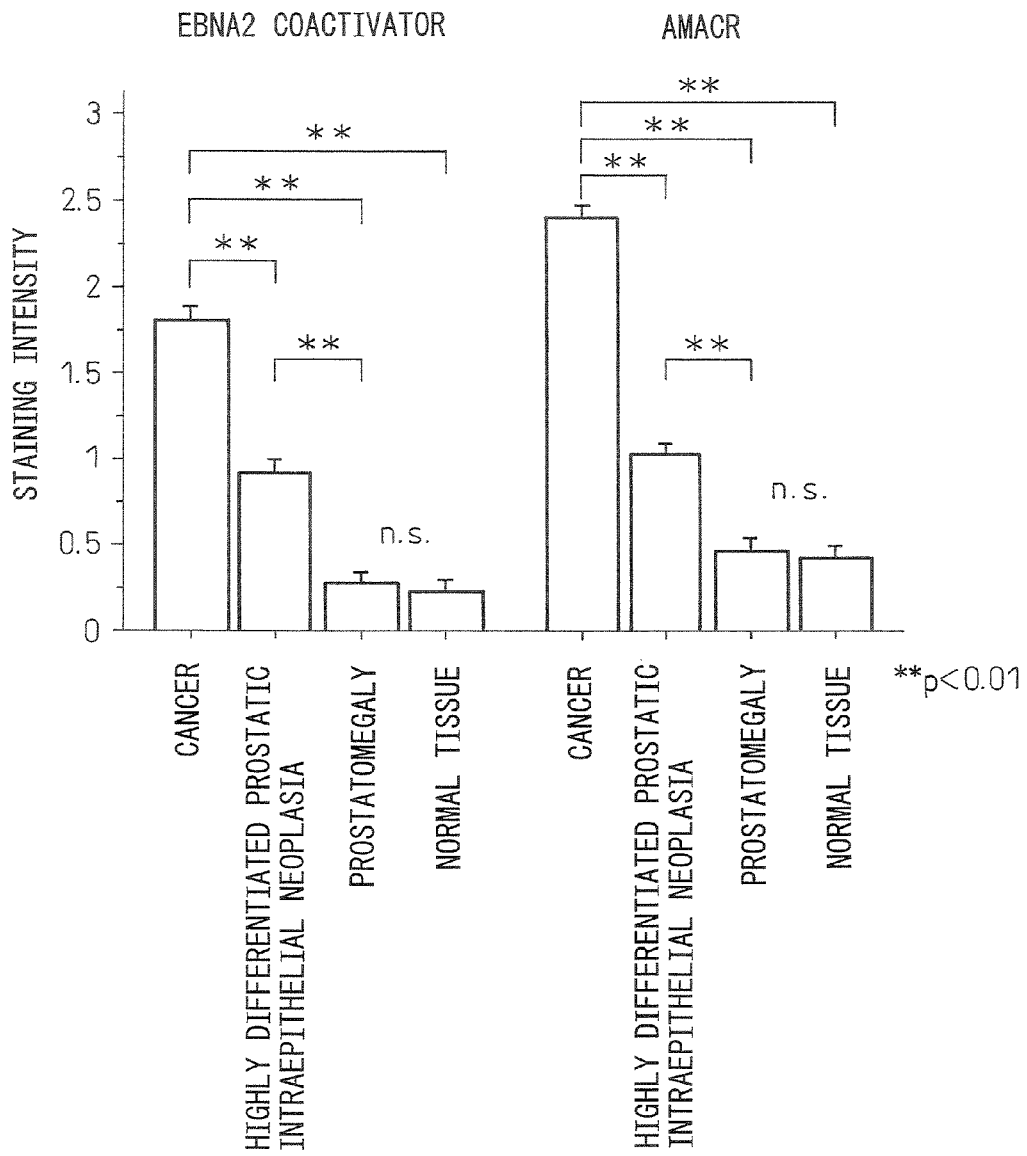
FIG. 10 shows the results of classifying stained images of prostate cancer tissue sites, highly differentiated prostatic intraepithelial neoplasia sites, prostatomegaly tissue sites and normal tissue sites according to staining intensity using EBNA2 coactivator p100 and AMACR antibodies.

The results of classifying stained images at prostate cancer tissue sites, highly differentiated prostatic intraepithelial neoplasia (high-grade PIN) sites, prostatomegaly tissue sites and normal tissue sites by staining intensity are shown in FIG. 10. Both EBNA2 coactivator p100 and AMACR exhibited a significant difference of $p<0.01$ for prostate cancer with respect to high-grade PIN, prostatomegaly and normal tissue. In addition, they also exhibited a significant difference of $p<0.01$ for high-grade PIN with respect to prostatomegaly and normal tissue.

Figure 11:
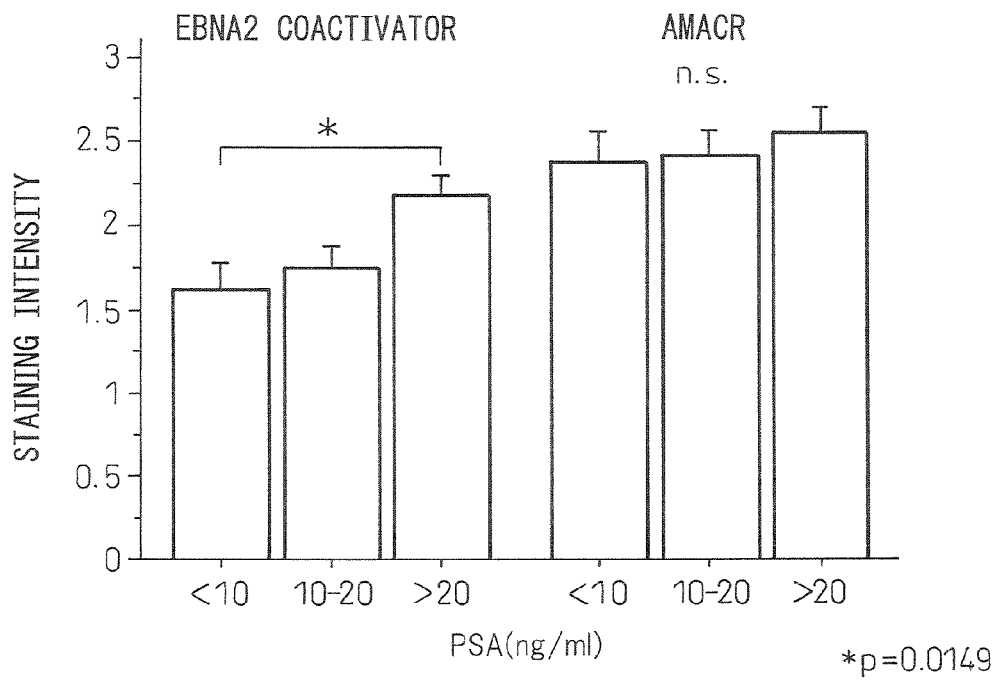
FIG. 11 shows the results of classifying staining intensity for specimens having a PSA concentration of less than 10 ng/mL, 10 to 20 ng/mL and greater than 20 ng/mL using EBNA2 coactivator p100 and AMACR antibodies.

The results of classifying specimens acquired from patients having PSA concentrations of less than 10 ng/mL, 10 to 20 ng/mL and greater than 20 ng/mL to demonstrate a correlation with staining intensity are shown in FIG. 11. In contrast to AMACR not exhibiting a significant causative relationship between staining intensity and PSA concentration, a significant increase in staining intensity dependent upon PSA concentration was observed for EBNA2 coactivator p100.

Figure 12:
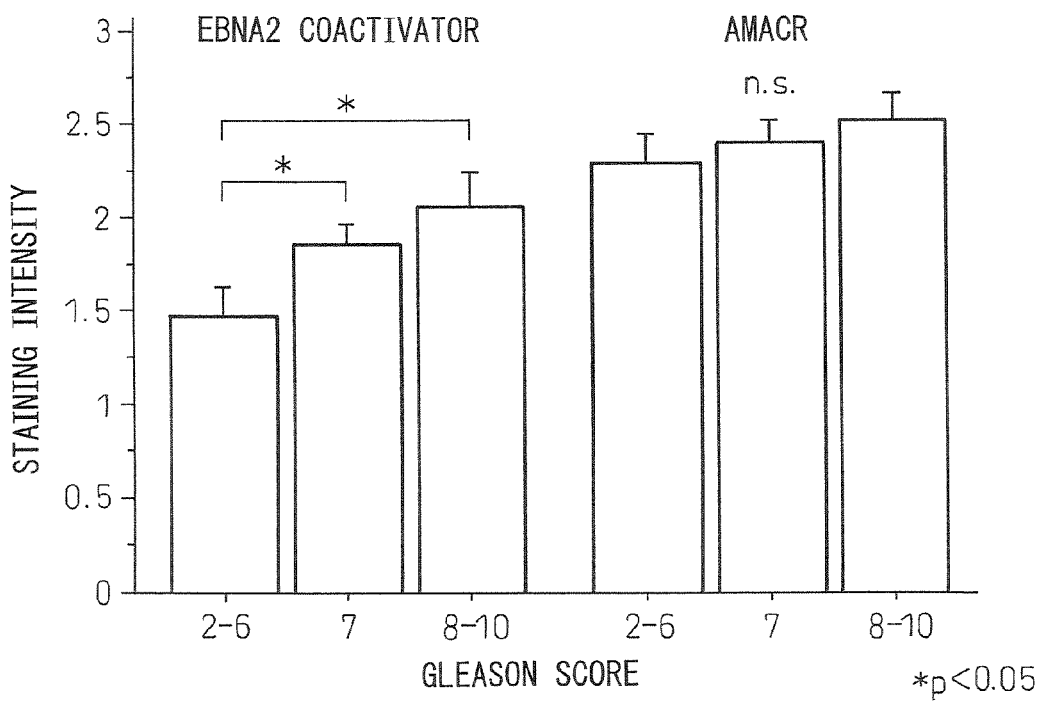
FIG. 12 shows the results of classifying staining intensity to a Gleason score of 2-6, 7 or 8-10 using EBNA2 coactivator p100 and AMACR antibodies.

The results of classifying Gleason scores into a score of 2-6, 7 or 8-10 to demonstrate a correlation with staining intensity are shown in FIG. 12. In contrast to AMACR not exhibiting a significant causative relationship between staining intensity and Gleason score, staining intensity was observed to increase dependent upon Gleason score for EBNA2 coactivator p100, with a significant difference of $p<0.05$ observed for Gleason scores of 7 or higher with respect to those of 2 to 6. In addition, pathological stained images of Gleason patterns 2 to 5 are shown in FIG. 13, and increases in staining intensity were observed as the patterns increased.

Figure 14:
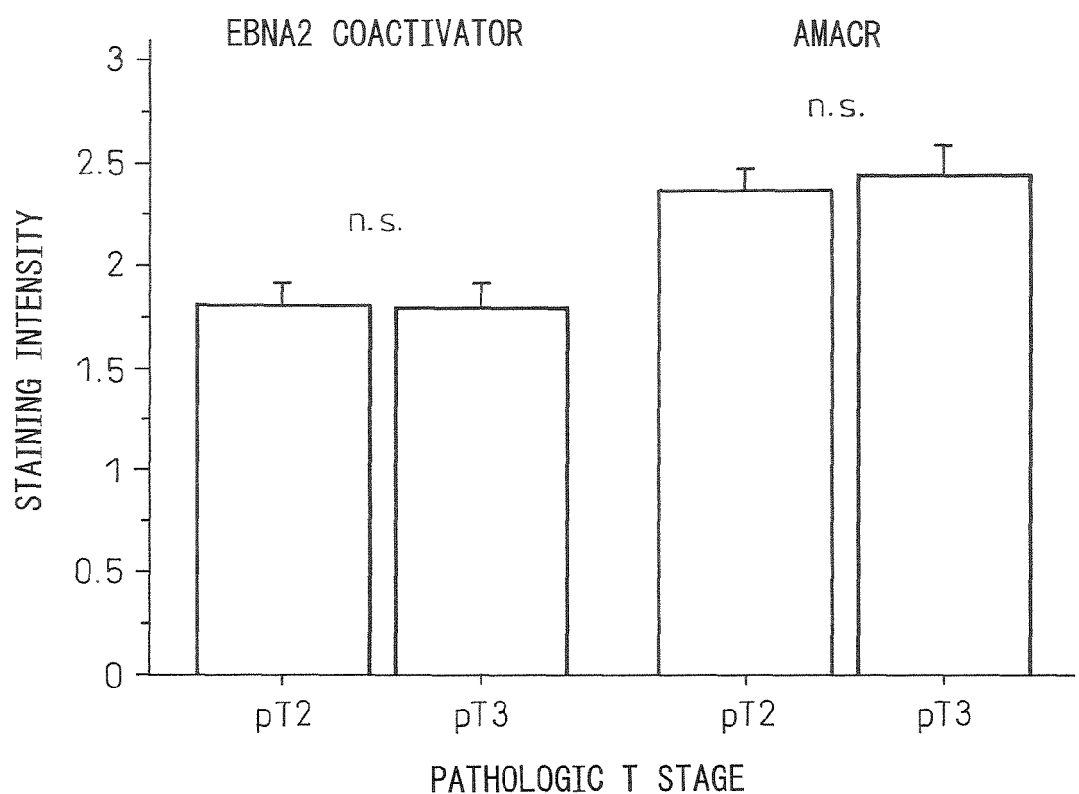
FIG. 14 shows the results of classifying staining intensity according to pathological T stage classifications of pT2 and pT3 using EBNA2 coactivator p100 and AMACR antibodies.

The results of demonstrating a correlation between staining intensity for pathological T stage classifications pT2 and pT3 are shown in FIG. 14. There were no differences observed in stained images between pT2 and pT3 for either EBNA2 coactivator p100 or AMACR.

Example 12

Reactivity to Various Cancer Tissues Using a Tissue Array

Figure 15:
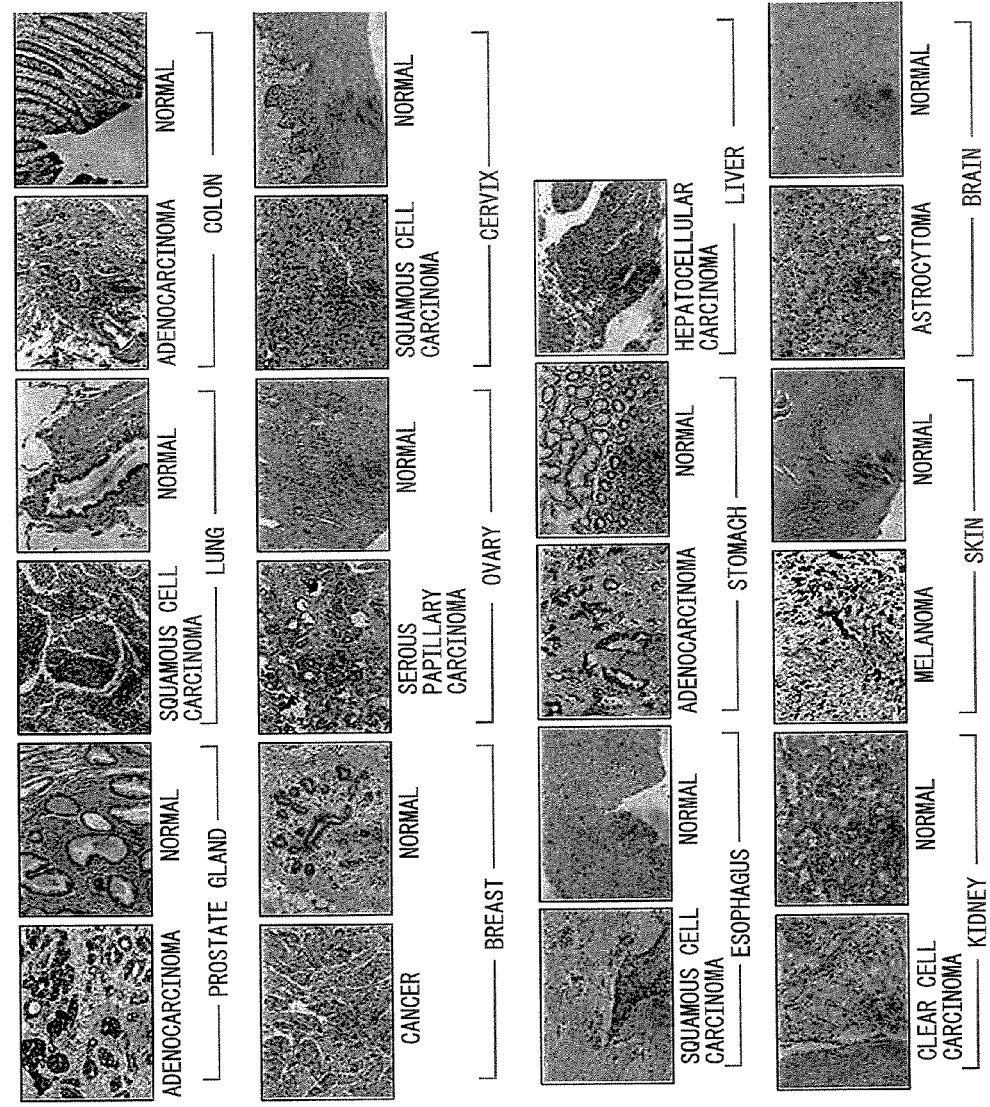
FIG. 15 shows staining results during immunohistochemical staining of various cancer tissues with EBNA2 coactivator p100 antibody using a tissue array.

Immunohistochemical staining was carried out on various cancer tissues in accordance with the method described in Example 6 using a tissue array (US Biomax Inc., Rockville, Md., USA). Stained images of various cancers of prostate gland, lung, colon, breast, ovary, cervix, esophagus, stomach, liver, kidney, skin and brain were observed as shown in FIG. 15. The results of classifying the staining intensity thereof in accordance with Example 11 are shown in FIG. 16. Staining intensity was classified as +2 in prostate cancer and colon cancer, and as +1 in lung cancer, gastric cancer, breast cancer, skin cancer and brain tumor, while stained images were not observed in ovarian cancer, esophageal cancer, cervical cancer, renal cancer and liver cancer.

Example 13

Antitumor Activity Test by siRNA

Figure 17:
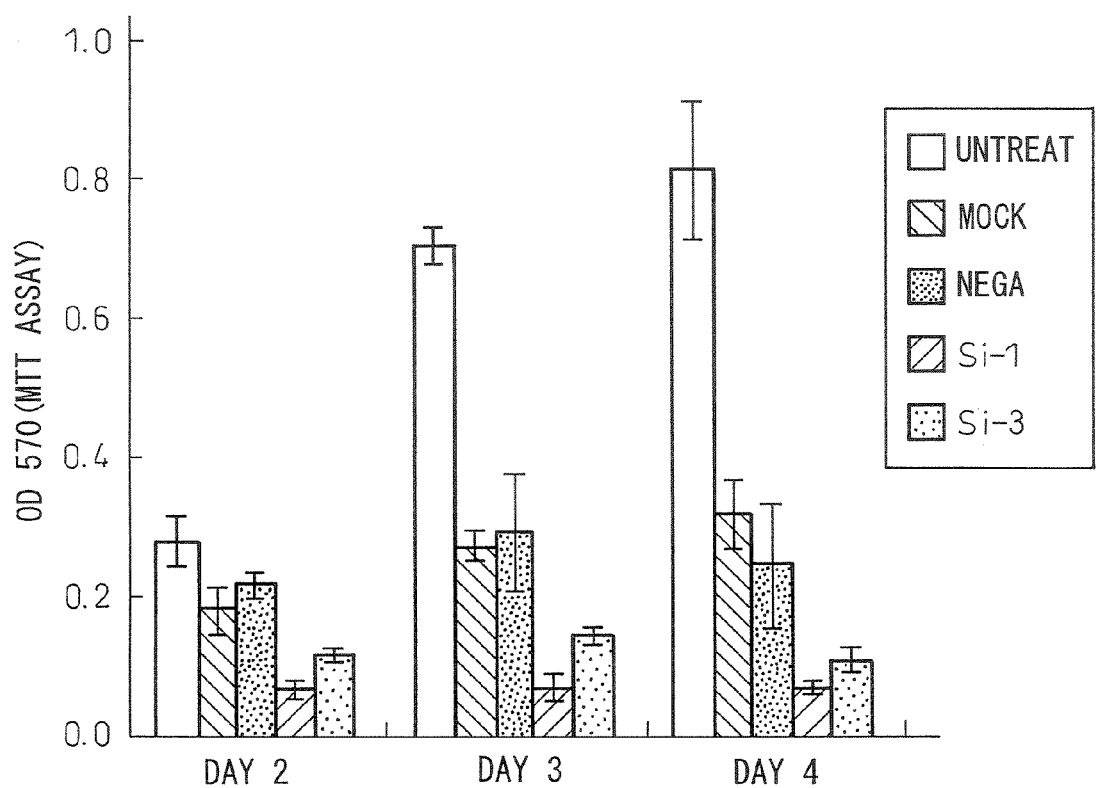
FIG. 17 shows the results of an anti-tumor activity test (MTT assay) using siRNA.

An antitumor activity test by MTT assay was carried out to determine whether or not it is possible to control cell proliferation of prostate cancer cell line PC3 using two types of siRNA. More specifically, PC3 cells were cultured in a 96-well plate at $5 \times 10^5$ cells/well followed by transfection of siRNA at 10 pmol/well using DharmaFECT™ 2 (GE Health Science) on the following day. After starting treatment with an untreated group, group in which the gene transfection procedure was carried out without using siRNA (mock group), group in which siRNA was used that is unrelated to this test (Nega group) and two groups using siRNA (Si-1 and Si-3), the survival rates of the cells were verified at an absorbance of 570 nm using MTT Assay (Chemicon International, Inc.) on days 2, 3 and 4. The sense and antisense sequences of Si-1 and Si-3 consisted of an Si-1 sense sequence of GGGAGAACACCCAGGAUAATT (SEQ ID NO. 11), an Si-1 antisense sequence of UUAUCCUGGGUGUUCUC-CCTT (SEQ ID NO. 11), an Si-3 sense sequence of CCG-CAAAGCAGAAGAAAGATT (SEQ ID NO. 11) and an Si-3 antisense sequence of UCUUUCUUCUGCUUUGCGGTT (SEQ ID NO. 11). As a result, cell proliferation was strongly inhibited in cells using Si-1 and Si-3 siRNA as shown in FIG. 17.

The invention claimed is:

1. A method for detecting prostate cancer, colon cancer, lung cancer, gastric cancer, breast cancer, skin cancer, and/or brain tumor in a subject, comprising
   obtaining a sample suspected of containing cancer cells from the subject;
   contacting the sample with an antibody which recognizes Epstein-Barr virus nuclear antigen 2 coactivator p100 (EBNA2 coactivator p100) and specifically binds to at least an amino acid sequence of RPASPATETVPAF-SERTC (SEQ ID NO. 1), an amino acid sequence DDDARTDAVDSVVR (SEQ ID NO. 2), or a partial sequence thereof;
   detecting a presence of a specific interaction between the antibody and an antigen in the sample and comparing that interaction to a control non-cancerous sample, wherein the presence of the interaction that is increased compared to the control non-cancerous sample is indicative of cancer in the subject wherein the cancer is an advanced cancer not an insignificant cancer.

2. The detecting method according to claim 1, wherein the antibody is monoclonal antibody.

3. The detecting method according to claim 1, wherein the antibody at least specifically binds to an amino acid sequence of SEQ ID NO. 1, or an amino acid sequence of SEQ ID NO. 2.

4. The detecting method according to claim 1, wherein the detecting comprises a method selected from the group consisting of a competitive method with an enzyme labeled antibody, isotope labeling of the antibody, fluorescent labeling of the antibody, a sandwich method, a homogeneous assay method with fluorescence polarization, and a binding assay with surface plasmon resonance analysis.

5. The detecting method according to claim 1, wherein the detecting comprises an immunohistochemical technique wherein the antibody is labeled with an enzyme, an isotope labeling or a fluorescent moiety.

6. The detecting method according to claim 1, wherein the sample comprises human cells, human tissue or an extract thereof.

7. The detecting method according to claim 1, wherein the cancer is prostate cancer.

* * * * *